United States Patent
Commereuc et al.

(10) Patent No.: US 6,444,866 B1
(45) Date of Patent: *Sep. 3, 2002

(54) SEQUENCE OF PROCESSES FOR OLEFIN OLIGOMERIZATION

(75) Inventors: Dominique Commereuc, Meudon; Alain Forestiere; François Hughes, both of Vernaison; Hélène Olivier-Bourbigou, Rueil Malmaison, all of (FR)

(73) Assignee: Institut Francais du Petrole, Rueil Malmaison Cedex (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/110,434

(22) Filed: Jul. 6, 1998

(30) Foreign Application Priority Data

Jul. 4, 1997 (FR) .............................. 97 08633

(51) Int. Cl.[7] .............................. C07C 2/02; C07C 2/06; C07C 2/26
(52) U.S. Cl. .................. 585/517; 585/523; 585/527; 585/531
(58) Field of Search .................. 585/517, 523, 585/527, 531

(56) References Cited

U.S. PATENT DOCUMENTS 4,740,645 A * 4/1988 Garwood et al. .......... 585/329
5,245,097 A * 9/1993 Wu .............................. 585/513
5,502,018 A * 3/1996 Chauvin et al. ............ 502/213

FOREIGN PATENT DOCUMENTS

FR 845108 8/1939

* cited by examiner

Primary Examiner—Thuan D. Dang
(74) Attorney, Agent, or Firm—Millen, White, Zelano & Branigan, P.C.

(57) ABSTRACT

A process for oligomerising olefins in an organic feed containing at least one olefin comprises two steps with different types of catalysis. The cut to be treated containing at least one olefin ($C_n$) is introduced via line 1 into a reaction zone R1 where in a first step it undergoes catalytic oligomerisation, either of a liquid phase homogeneous type, or heterogeneous with a solid support. The effluent produced is sent via line 2 to a heat exchanger E1 traversed by a cold liquid. The effluent is thus cooled before being sent via line 3 to a second reaction zone R2 where it undergoes catalytic oligomerisation in a liquid-liquid two-phase medium. After reaction, the effluent is fed via line 4 to a zone L1 where it is washed. After washing, the hydrocarbon fraction is sent via line 5 to separator S1. The fraction containing the unreacted olefins ($C_n$) is separated from the oligomer product fraction produced, this fraction $C_n$ is evacuated from the apparatus via line 6, and the fraction containing the oligomer products is evacuated via line 7.

26 Claims, 4 Drawing Sheets

SEQUENCE OF PROCESSES FOR OLEFIN OLIGOMERIZATION

BACKGROUND OF THE INVENTION

The field of olefin transformation has been widely studied and is the subject of a number of patents. Particularly important processes are those which enable long chain oligomers to be produced. Depending on the number of carbon atoms in the chain, such oligomers have applications in the chemicals and petrochemicals industries, or are components of gasoline. The reactions which are of interest in the present invention are dimerization, co-dimerization or oligomerization of olefins.

The prior art contains numerous patents. Of those, we shall describe patents in which the catalysis reaction is carried out in a homogeneous liquid phase with a soluble catalyst, or heterogeneous catalysis is carried out with a solid catalyst. Such processes have disadvantages, however: the catalysts used—often nickel based—are expensive. Solid catalysts deactivate by the action of pollutants, and they must be regularly regenerated or replaced. For soluble catalysts, the outlet effluent contains catalyst which must be separated out, involving unavoidable supplemental expense. In addition to the degree of conversion, which varies depending on the olefin to be treated—for n-butenes, the maximum degree of conversion of economic interest is 80%—, the reaction is generally not sufficiently selective; finally, a mixture of products is obtained—which is not always desirable—and which must be separated out.

SUMMARY OF THE INVENTION

The present invention uses a sequence of processes to carry out dimerization, co-dimerization or oligomerizing olefins in two steps. In the remainder of the text, the term "oligomerization" covers these three types of reactions.

The first step is catalytic oligomerization which may be of the homogeneous liquid phase type or of the heterogeneous type. The term "heterogeneous catalysis reaction" used in this text defines a reaction where two phases co-exist, the catalyst being solid. The second step is catalysis in a two-phase medium where the catalyst is dissolved in a polar phase which is not miscible with the organic phase containing at least one olefin. Among the advantages of this invention are a large increase in the reaction yield, and an increase in selectivity, so the reaction can be better oriented towards the species which are to be obtained. The second step of the reaction is particularly selective for dimers, which is the species which is most frequently desired. The invention also enables the pollutants present in the apparatus to be closely controlled, as any pollutants present in the initial feed will have been partially eliminated in the first step. If necessary, they can also be completely eliminated by an intermediate treatment. In a particular implementation of the invention, catalyst wastage can be reduced by better use of the catalyst in the two-phase medium. The first step of the process is thus homogeneous catalysis in which at least part of the catalyst is recovered with the effluent. The catalyst is then used in the liquid-liquid two-phase catalysis step.

Processes for homogeneous liquid phase catalysis or heterogeneous catalysis can convert feeds containing olefins, particular propylene or n-butenes. These processes can treat feeds containing 50% to 100% by weight of olefins, usually 70% to 90% by weight. However, these processes are not limited to the treatment of these feeds alone, in particular it has been verified that they also work for feeds containing olefins with a carbon chain containing two, five or six carbon atoms. For feeds containing less than 50% by weight of olefins, in particular for propylene or n-butenes, the consumption of catalyst or the size of the reactors renders the process less economical, the costs being higher as the feed becomes more diluted and the olefin less reactive. Similarly, the cost is large for olefins with a carbon chain containing more than four carbon atoms, which is why such homogeneous liquid phase catalysis or heterogeneous catalysis processes are particularly suitable for olefins containing three or four carbon atoms. Further, the selectivity for dimers—which is the product which is most in demand—strictly depends on conversion: for butenes, it does not exceed 85% for a feed converted in an amount of 80% by weight. The liquid-liquid two-phase process can convert dilute feeds, i.e., containing less than 50% by weight of olefins, and can also produce a higher selectivity for dimers, this selectivity possibly reaching 95%; further, this liquid-liquid two-phase process renders the conversion to dimers less dependent on the starting feed.

Prior art heterogeneous catalysis processes which can be used in the first step of the invention use catalysts containing a metal, preferably nickel, on a to support which can, for example, be alumina, silica, silica-alumina, a zeolite or a silico-aluminate. The reaction temperature is about 10° C. to 250° C., the pressure being such that the feed remains liquid. French patent French application No. 2,608,594 describes a process for dimerizing olefins using heterogeneous catalysts comprising nickel compounds deposited on alumina. The heterogeneous catalysis catalysts in the first step of the invention can also be a mineral compound alone, the mineral compound being, for example, a silico-aluminate, a zeolite or a silica-alumina. IFP Enterprises markets a silica-alumina compound under trade reference IP501, for example.

Prior art descriptions concerning homogeneous liquid phase processes propose the use of different types of catalysts depending on the olefins to be treated and also depending on the product which is particularly desired, those catalysts all containing at least one compound of a metal, preferably nickel, and an alkoylaluminium halide. The reaction temperature is about −40° C. to +100° C., the pressure is such that the reactants are at least partially, normally mainly in the liquid phase and the stirring conditions are those necessary to convert at least a portion of the feed.

For oligomerization, in particular dimerization and trimerization, of olefins, United States patent U.S. Pat. No. 4,316,851 recommends the use of mixed nickel compounds with general formula $(R_1COO)(R_2COO)Ni$ where $R_1$ is an alkyl, cycloalkyl, alkenyl, aryl, aralkyl or alkaryl residue, for example, containing at least 5 carbon atoms, preferably an alkyl residue containing 5 to 20 carbon atoms, this residue possibly being substituted by hydroxyl groups, for example, and $R_2$ is a halogenoalkyl residue containing 1 to 3 carbon atoms, with formula $C_mH_pX_q$ where m=1, 2 or 3, p equals zero or a whole number and q is a whole number, with the condition that p+q=2m+1. $R_2$ is preferably a halogenomethyl residue $CX_nH_{3-n}$ where X is fluorine, chlorine, bromine or iodine, and n is a whole number from 1 to 3.

The preparation of catalysts for dimerization or co-dimerizing $C_2$, $C_3$ or $C_4$ olefins is also well known, the catalysts resulting, for example, from the interaction of halides of π-allyl nickel phosphine with Lewis acids (French application No. 1,410,430), from the interaction of halides of nickel phosphine with Lewis acids (U.S. Pat. No. 3,485,881) or from the interaction of certain nickel carboxylates with alkylaluminium halides (U.S. Pat. No. 3,321,546). Similarly, U.S. Pat. No. 4,404,415 describes dimerizing propylene to higher oligomers: nonenes or mixtures of nonenes and dodecenes, the type of catalyst used being a complex in which a metal, preferably nickel, is bonded to at least one unsaturated hydrocarbon residue, which may or may not be substituted, for example a bis-π-allyl nickel, a π-allyl nickel halide or bis-cyclooctadiene nickel associated with a halogenated aluminum compound. A further catalyst type is constituted by complexes formed by mixing at least one nickel compound with at least one alkylaluminum compound and possibly a ligand, for example a phosphine. A preferred class of catalysts comprises catalysts obtained by mixing at least one nickel carboxylate (the carboxylate residue containing at least six carbon atoms) with at least one dichloroalkylaluminum or alkylaluminum sesquichloride, the Al/Ni atomic ratio being in the range 2:1 to 50:1.

However, depending on the impurities present in the feeds to be treated, difficulties in industrial implementation may be encountered. Such difficulties have been overcome in part by using catalysts with improved catalytic formulae incorporating at least one divalent nickel compound with at least one alkylaluminium halide and at least one organic Brønsted acid (U.S. Pat. No. 4,283,305) or a mixed compound of nickel in association with an alkylaluminum compound (U.S. Pat. Nos. 4,316,851; 4,366,087; and 4,389,049). These improved catalytic formulae usually include a halogenocarboxylic acid, the corresponding anion or a carboxylic acid anhydride as in the case of U.S. Pat. No. 4,362,650. In addition to extolling the virtues of the catalysts described above, U.S. Pat. No. 5,059,571 proposes to overcome the difficulties of implementing the process by using a catalyst comprising at least one divalent nickel compound with at least one alkylaluminium halide and at least one epoxy compound.

A further type of catalyst used exhibits good results for dimerizing butenes and is described in U.S. Pat. No. 4,716,239 as the association of an inorganic divalent nickel compound (for example a carbonate, bicarbonate, or a basic carbonate (hydroxycarbonate), a hydroxide (or oxide) with a halogenoacetic acid (for example monochloroacetic acid, monofluoroacetic acid, dichloroacetic acid, trichloroacetic acid, difluoroacetic acid or trifluoroacetic acid) in a carboxylic acid ester with general formula $R_1COOR_2$ where $R_1$ and $R_2$ are each a linear or branched alkyl group containing 1 to 5 carbon atoms, $R_1$ also possibly being hydrogen. Such esters of acids can, for example, be methyl acetate, methyl formate, n-butyl acetate, isobutyl acetate, methyl propionate, or isopropyl formate.

The subject matter of our invention is a two-step process. When the first step involves catalysis in a homogeneous phase reaction zone, one of the catalysts described above is used. The catalyst selected depends on the olefin to be treated and on the product which is to be obtained in the majority. However, the first step can also be oligomerization by heterogeneous phase catalysis. In this type of catalysis, nickel compounds deposited on mineral supports or the supports alone are generally used. Such catalysts have the disadvantage, however, of being less selective for dimers, in particular when conversion is high, the amount of trimers and tetramers possibly representing over 30% of the products. Thus the invention described in French application No. 2,608,594 is a process for producing improved catalysts comprising nickel compounds deposited on alumina. One advantage of supported catalysis processes is that the solid catalyst remains in the reactor, and the problem of separating the catalyst from the effluent does not have to be addressed. In contrast, it cannot be used as a catalyst in the second step in the sequence of processes of the invention, as is possible when a soluble catalyst is used for homogeneous liquid phase catalysis.

The second step of the process of the invention is two-phase catalysis where the catalyst is dissolved in a polar phase which is not miscible with the organic phase containing the olefins.

These catalytic reactions in a two-phase medium are carried out at a temperature of less than +100° C., for example between −50° C. and +100° C., the pressure being kept between 0.01 and 20 MPa, with the highest pressures being used for ethylene.

The documents cited above, in particular French patent French application No. 2,611,700, describe the use of liquids with an ionic nature, compositions of which we shall describe below, used as solvents for the organometallic nickel complexes for olefin dimerization. The use of such media which are only very slightly miscible with aliphatic hydrocarbons enables the homogeneous catalysts to be put to better use. In order to carry out these oligomerizations, the olefin is brought into contact with the polar phase containing the nickel complex and contact between the phases is ensured by energetic stirring. At the end of the reaction, the phases are separated by any suitable means, for example the mixture is allowed to settle and the upper phase, which includes the dimers, co-dimers and oligomers, is extracted. The medium can also be supplied continuously and the phase containing the dimers and oligomers can be extracted continuously, taking care to provide a zone within the reactor which enables the two liquid phases to be separated out. Olefins which can be treated by this type of process are, for example, ethylene, propylene, 1- and 2-butenes, styrene, pentenes or mixtures of these compounds.

Among the different compositions of the polar phase and dimerization, co-dimerization and oligomerization catalytic compositions are the examples in the following patents: French application No. 2,611,700 concerns a medium with an ionic nature, liquid at the usual dimerization temperatures, which comprises at least one aluminum halide and at least one quaternary ammonium halide. The nickel complexes which are known for dimerizing, co-dimerizing and oligomerizing olefins and which are soluble in the media with an ionic nature can be neutral zero-valent, monovalent or divalent complexes, these latter must contain at least one nickel-carbon or nickel-hydrogen bond, or ionic complexes containing a nickel-carbon or nickel-hydrogen bond. The description in U.S. Pat. No. 5,104,840 has a non aqueous liquid composition with an ionic nature resulting from bringing at least one alkoylaluminium dihalide into contact with at least one quaternary ammonium halide and/or at least quaternary phosphonium halide. The composition is liquid below about +80° C., for example between about −70° C. and about +40° C. The compounds in the composition can be mixed in any order. The mixture can be made by simply bringing the compounds into contact followed by stirring, until a homogeneous liquid phase is obtained. The mixture can also advantageously be made in the presence of a saturated aliphatic hydrocarbon solvent which dissolves the alkoylaluminium dihalide(s), for example, in this case, after producing two clear liquid phases, the supernatant phase containing essentially the hydrocarbon solvent is eliminated in order to allow only the liquid composition to subsist. Any nickel complex can be used as a catalyst in a composition with an ionic nature. U.S. Pat. No. 5,550,306 and U.S. Pat. No. 5,502,018 describe processes for dimerization, codimerization and oligomerizing olefins, in particular propylene, but these processes can be used on ethylene, n-butenes and n-pentenes, alone or as a mixture, pure or diluted by an alkane, such as those found in cuts from oil refining processes such as catalytic cracking or steam cracking. In the process for dimerization, co-dimerization and oligomerizing at least one olefin, the compounds are brought into contact in any order. The reaction temperature can be in the range −40° C. to +70° C., preferably in the range −20° C. to +50° C., the pressure can be in the range from atmospheric pressure to 20 MPa, preferably in the range from atmospheric pressure to 5 MPa. The composition described in U.S. Pat. No. 5,550,306 results from dissolving a nickel compound mixed or complexed with at least one tertiary phosphine, at least partially dissolved in a liquid mixture with an ionic nature of a quaternary ammonium halide and/or a quaternary phosphonium halide, an aluminium halide, an aromatic hydrocarbon and possibly an alkylaluminium. More precisely, the catalytic composition comprises at least one nickel compound mixed or complexed with at least one tertiary phosphine, at least partially dissolved in a medium with an ionic nature resulting from bringing at least one aluminium halide into contact with at least one quaternary ammonium halide and/or at least one quaternary phosphonium halide and with at least one aromatic hydrocarbon. The composition described in U.S. Pat. No. 5,502,018 results from mixing one equivalent of a divalent nickel complex containing two molecules of a tertiary phosphine with one equivalent of a divalent nickel complex containing neither water nor phosphine. The mixture of two types of nickel compounds must necessarily be associated with an alkylaluminium halide, the mixture being used in conventional implementations of the reaction, i.e., without solvent or in the presence of a halogenated or non halogenated hydrocarbon. These mixtures are particularly useful in the liquid compositions with an ionic nature which are formed by quaternary ammonium halides, and/or quaternary phosphonium halides with aluminium halides and possibly aromatic hydrocarbons. The latest research described in French application No. 2,736,562 regarding processes for oligomerizing olefins in a two-phase medium have a catalytic composition comprising a mixture of a lithium halide, an alkylaluminium halide and at least one compound of a catalytic element, in particular a nickel complex, and at least one hydrocarbon phase. This mixture has the advantage of being liquid at the start of the reaction and of gradually being transformed into a solid which can easily be separated from the hydrocarbon phase. The olefins to which the process can be applied are, for example, ethylene, propylene, n-butenes, and n-pentenes, alone or as a mixture. The olefin(s) can be used pure or diluted with saturated hydrocarbons such as those found in the cuts from various hydrocarbon refining processes, such as ethane with ethylene, propane with propylene, butanes with butenes. The reaction temperature will be in the range −30° C. to +100° C., preferably in the range −10° C. to +50° C. The pressure can be in the range from atmospheric pressure or below atmospheric pressure to 10 MPa, preferably in the range from atmospheric pressure to 1 MPa, but this pressure will be sufficient to keep at least a portion of the olefin or olefins in the liquid phase.

The first catalytic oligomerization step of the process of the invention is preferably liquid phase homogeneous catalysis or heterogeneous catalysis with a solid catalyst. The type of catalysis and the catalyst selected depend on the olefin or olefins to be treated and on the product or products which are to be obtained as the major product. As described above, for homogeneous liquid phase catalysis, the catalytic composition is preferably as follows: the catalyst is a nickel compound or a mixture of nickel compounds, the co-catalyst is an alkyl aluminium or a mixture of alkyl aluminium compounds, or a halogenoalkyl aluminium or a mixture of halogenoalkyl aluminium compounds, or a halogenoacetic acid or a mixture of halogenoacetic acids, and the optional additive to the catalyst may be a compound with an acidic nature, the anion corresponding to that acid, a carboxylic acid ester, an epoxy compound or a phosphine. The catalysts, co-catalysts and possible additives are introduced into the reactor in which the internal temperature is about −40° C. to +100° C., the pressure is such that the reactants are kept at least partially, usually mainly, in the liquid phase, and the stirring conditions are so as to convert at least a portion of the feed. Energetic mechanical stirring is applied to obtain maximum oligomer conversion. After this first reaction step, the oligomers obtained can be isolated and/or the catalyst can be inhibited and/or the effluent can be washed.

BRIEF DESCRIPTION OF THE DRAWINGS

The apparatus of FIG. 4 is used, as is preferably, when the first step is a heterogeneous type catalytic oligomerization reaction using a solid support.

Figure 1:
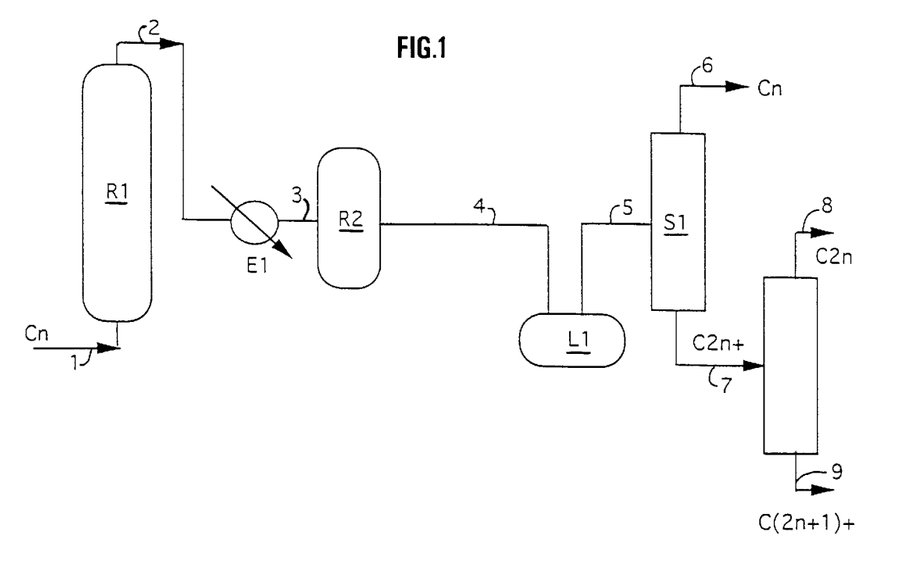
FIG. 1 shows the case of oligomerization without any treatment between the two steps. All of the effluent leaving the reaction zone from the first step—and optionally the liquid catalyst used in the first step—enters the reaction zone for the second step.
Figure 2:
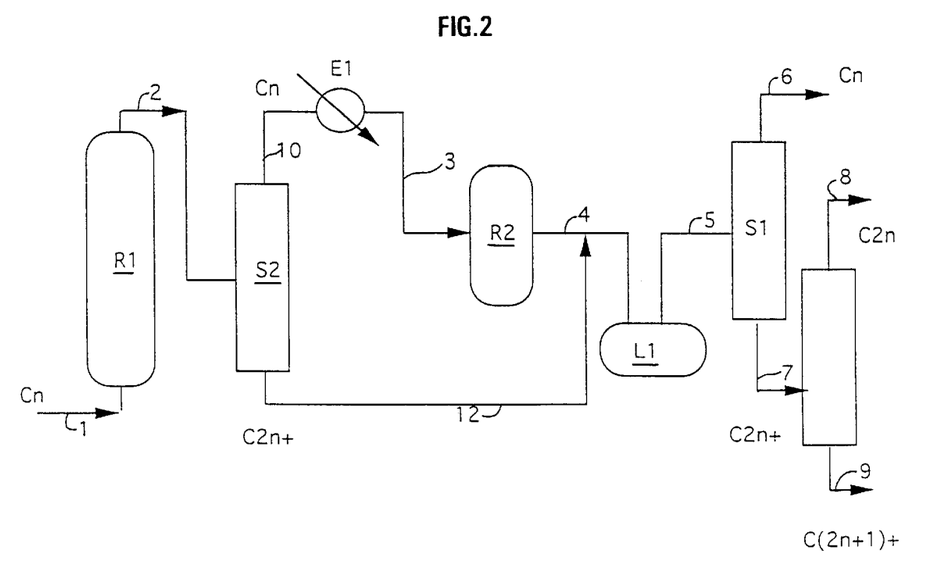
In FIG. 2, the products obtained from the first step are isolated from the unreacted species, these species undergoing the second step reaction. The oligomers produced in the first step and those produced in the second step are then combined and washed. If all of the effluent is washed after the first step, this effluent must then be dried before carrying out the liquid-liquid two-phase medium catalysis (FIG. 3). The term "washing" means treatment using an aqueous, preferably basic, solution, but acid solutions are also envisagable, optionally followed by water washing.
Figure 3:
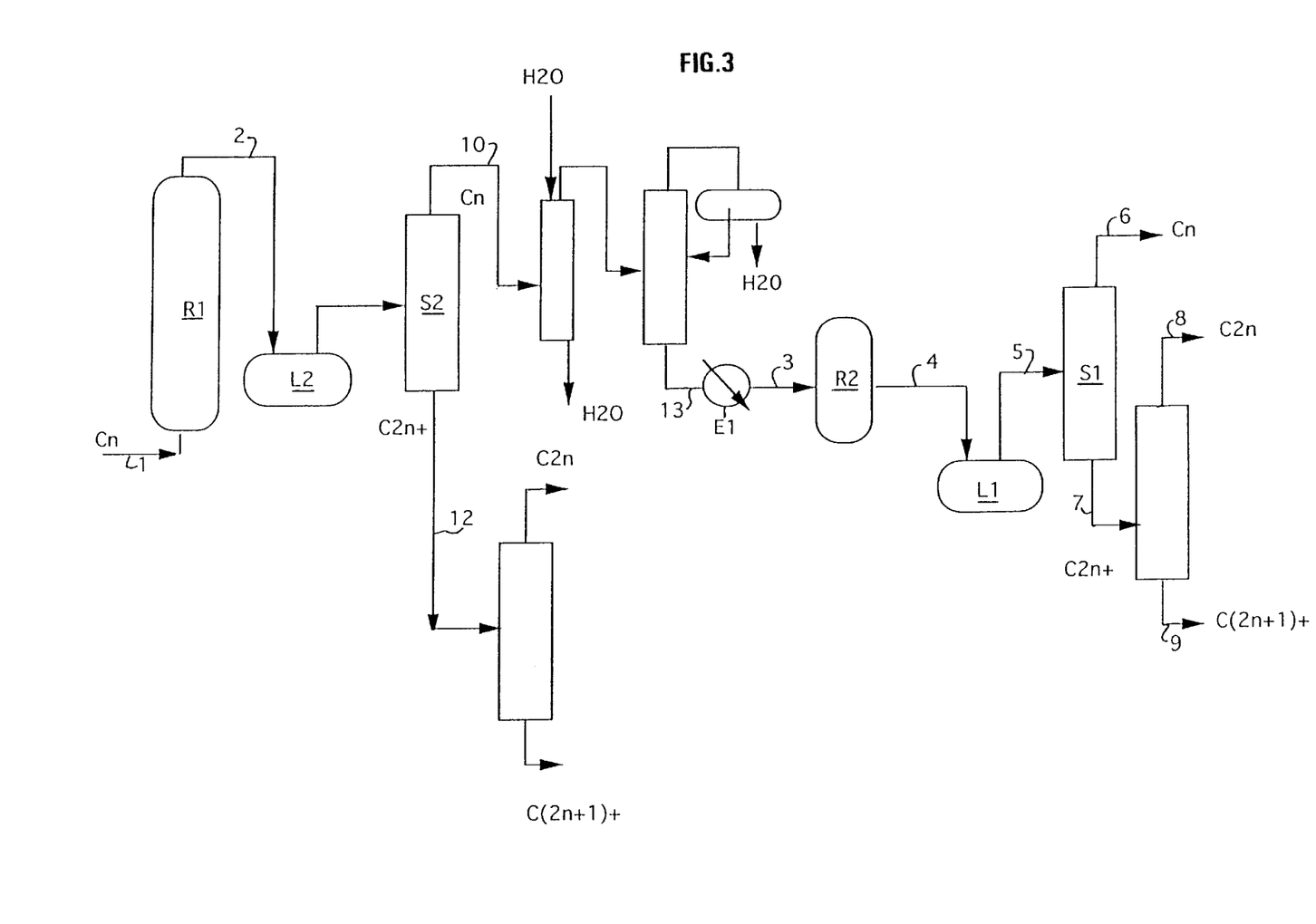
Figure 4:
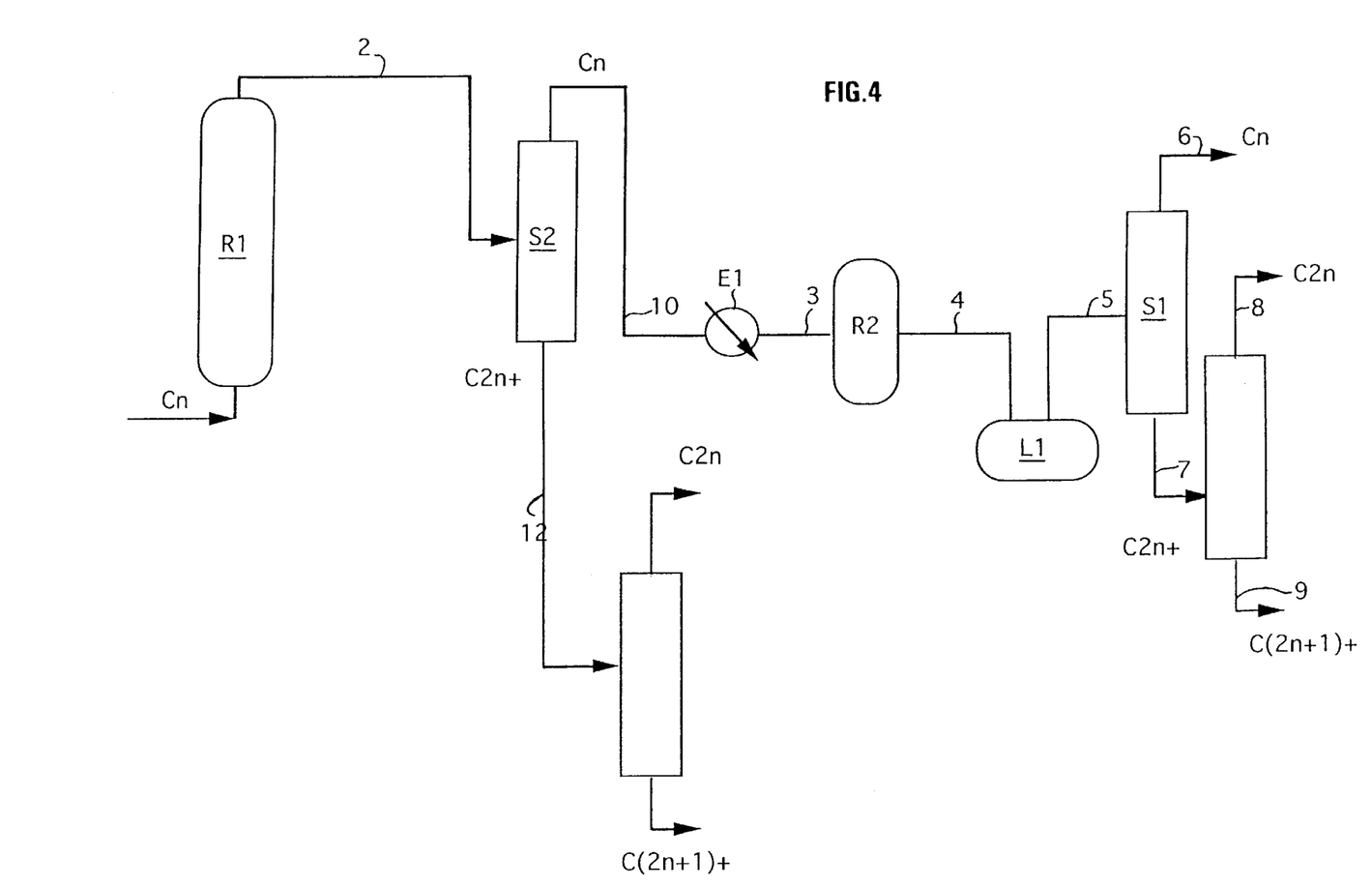

When the first step is heterogeneous catalysis, the reaction temperature is about +10° C. to +250° C., preferably about +30° C. to +100° C., the pressure is kept such that the feed is at least in part, usually mainly, in the liquid state. After heterogeneous catalysis, no washing prior to the liquid-liquid two-phase catalysis is necessary (FIGS. 1 and 4). However if, in one particular implementation, it appears to be wise to isolate the oligomers obtained or to wash the effluent from the first step, a treatment may be provided (washing the effluent, separating the effluent constituents, removing pollutants) between the two steps of the process (FIGS. 2 and 3).

The second step of the process of the invention is liquid-liquid two-phase oligomerisation. The reactant medium is a medium with an ionic nature which is not or is only slightly miscible with the organic phase containing at least one catalyst which is usually a nickel complex or a mixture of a nickel complex and optionally at least one catalyst additive. The polar phase can also be a medium with an ionic nature which is not miscible with the organic phase which does not contain the catalyst, the catalyst from the liquid-liquid two-phase medium oligomerization reaction is thus the catalyst used in the first step (in this case, the first step is homogeneous catalysis). The catalyst is then introduced into the reactor with the effluent leaving the first step reactor.

The ionic medium comprises at least one salt with formula $Q^+A^-$, where $Q^+$ is a quaternary ammonium or phosphonium cation or a mixture of the two or a lithium cation, and $A^-$ is a coordinating or non co-ordinating anion, selected from the group formed by halogenoaluminates, organohalogenoaluminates, organogallates, organohalogenogallates or a mixture of at least two of these compounds.

Figure 5:
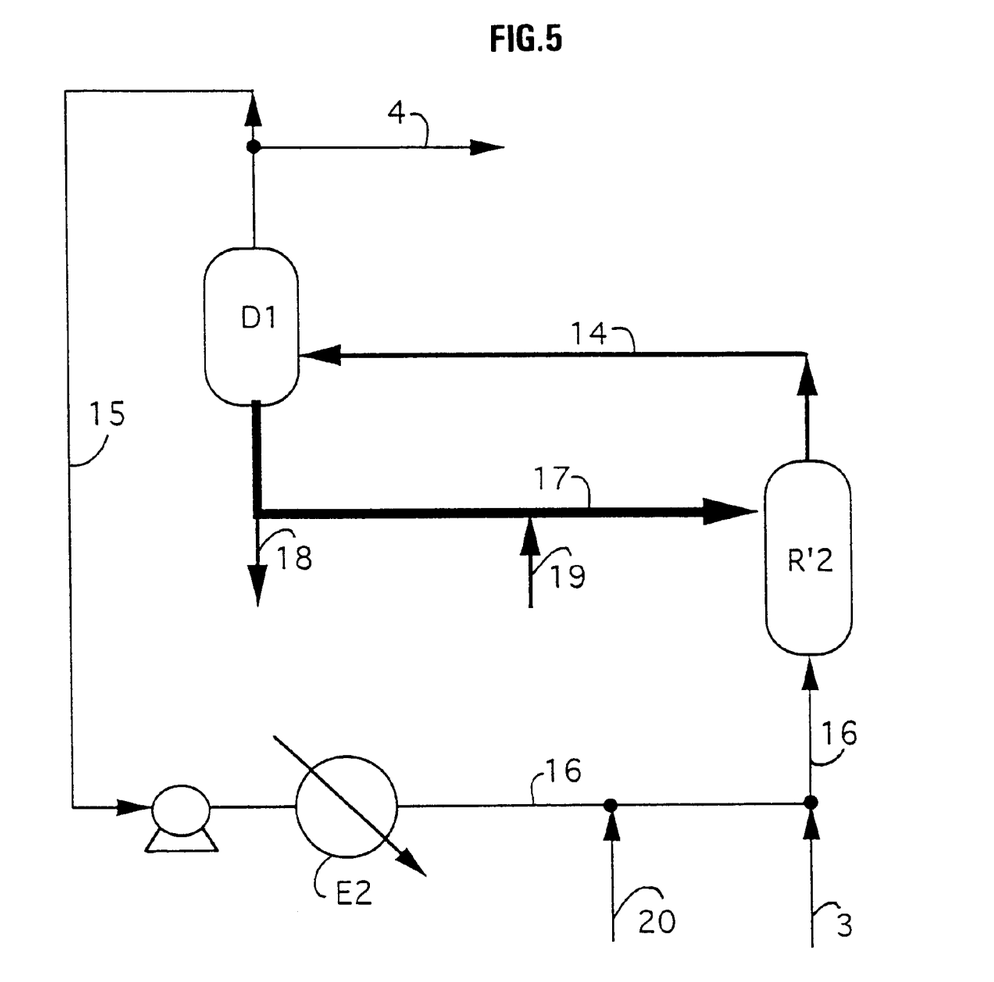
FIG. 5 shows a detail of reaction zone $R_2$ where liquid-liquid two-phase medium catalytic oligomerization is carried out.

After injecting the feed to be treated, a two-phase medium is obtained which must be vigorously stirred to ensure good contact between the two phases, this contact being necessary to obtain a good degree of conversion to oligomers. In one implementation which provides good yields, recycling the mixture of two reaction liquids causes some of the stirring: thus the emulsion contained in the reactor is continuously extracted and settled. After settling, two phases are obtained: the supernatant organic phase is isolated then cooled using a heat exchanger. Cooling enables the temperature in the reactor to be kept constant and avoids damaging the catalyst, by continuous control. A quantity of fresh polar phase equal to the quantity of polar phase which is extracted and settled is injected into the reactor. FIG. 5 shows the simplest apparatus for liquid-liquid two-phase catalysis.

After this liquid-liquid two-phase catalysis, the effluent leaving the reactor is washed with a basic solution then with water, and the oligomers obtained are isolated. This washing can optionally be together with washing, if it takes place, of the oligomers produced during the first step.

FIGS. 1 to 4 describe the most preferred implementations of the sequence of processes of the invention, however this does not limit the scope of the invention.

FIG. 1 describes the simplest implementation. The feed introduced comprises olefins containing n carbon atoms ($C_n$); n is generally 2, 3, 4, 5 or 6. The desired product in this case is the dimer ($C^{2n}$). The expression $C_{(2n+1)}^+$ represents the olefins produced which have a carbon chain which is longer than that of the desired dimer.

The cut to be treated containing at least one olefin ($C_n$) is introduced via line 1 into reaction zone $R_1$ where in a first step it undergoes catalytic oligomerization, either of the homogeneous liquid phase type, or of the heterogeneous type with a solid support. The effluent produced is sent via line 2 to a heat exchanger $E_1$ traversed by a cold liquid. The effluent is thus cooled before being sent to a second reaction zone $R_2$ via line 3 where it undergoes liquid-liquid two-phase catalytic oligomerization. After reaction, the effluent is sent via line 4 to a zone $L_1$ where it is washed. After washing, the hydrocarbon fraction is sent via line 5 to separator $S_1$. The fraction containing the unreacted olefins ($C_n$) is separated from the fraction of product oligomers, this fraction $C_n$ is evacuated from the apparatus via line 6. If a mixture of oligomers is obtained after the reaction, this last fraction is sent via line 7 to a zone where it undergoes a second separation step to isolate the desired products (recovered via line 8) from the $C_{(2n+1)}^+$ mixture evacuated via line 9.

FIG. 2 describes the case where the feed contains olefins containing n carbon atoms ($C_n$); n is generally 2, 3, 4, 5 or 6. In this case, the desired product is the dimer ($C_{2n}$). The expression $C_{(2n+1)}^+$ represents the olefins produced which have a carbon chain which is longer than that of the desired dimer.

In the implementation of FIG. 2, the cut to be treated containing at least one olefin ($C_n$) is introduced via line 1 into reaction zone $R_1$ where in a first step it undergoes catalytic oligomerization, either of the homogeneous liquid phase type, or of the heterogeneous type with a solid support. After the first reaction, the effluent is separated. The overhead fraction containing the unreacted olefins is separated from the fraction of oligomer products using a separator $S_2$. The overhead fraction is sent via line 10 to a heat exchanger $E_1$ traversed by a cold liquid. After cooling, the effluent is sent to a second reaction zone $R_2$ via line 3 where it undergoes liquid-liquid two-phase catalytic oligomerization. Before washing the effluent from the second step(in zone $L_1$), the phase of oligomers produced in the first step and sent via line 12 is added. After washing, the hydrocarbon fraction is sent to separator $S_1$ via line 5. The fraction containing the unreacted olefins ($C_n$) is separated from the fraction of product oligomers, and this fraction $C_n$ is evacuated from the apparatus via line 6. If after reaction a mixture of oligomers is obtained, this last fraction is sent via line 7 to a zone where it undergoes a second separation step to isolate the desired products (recovered via line 8) from the $C_{(2n+1)}^+$ mixture evacuated via line 9.

FIG. 3 describes the case where the feed contains olefins containing n carbon atoms ($C_n$); n is generally 2, 3, 4, 5 or 6. In this case, the desired product is the dimer ($C_2$). The expression $C_{(2n+1)}^+$ represents the olefins produced which have a carbon chain which is longer than that of the desired dimer.

In FIG. 3, the cut to be treated containing at least one olefin ($C_n$) is introduced via line 1 into reaction zone $R_1$ where in a first step it undergoes catalytic oligomerization, either of the homogeneous liquid phase type, or of the heterogeneous type with a solid support. The effluent is sent to a zone $L_2$ via line 2 where it is washed then the unreacted species are separated from the oligomer products using a separator $S_2$. If a mixture of oligomers is obtained, the desired product still has to be separated from the mixture; it is sent to a second separator via line 12. The overhead fraction leaving separator $S_2$ is sent via line 10 to a zone where it is water washed then dried. It is then sent via line 13 to a heat exchanger $E_1$ traversed by a cold liquid. The effluent is thus cooled before being sent to a second reaction zone $R_2$ via line 3 where it undergoes liquid-liquid two-phase catalytic oligomerisation. After reaction, the effluent is sent to a zone $L_1$ via line 4 where it is washed. After washing, the hydrocarbon fraction is sent via line 5 to separator $S_1$. The fraction containing the unreacted olefins ($C_n$) is separated from the fraction of product oligomers, this fraction $C_n$ is evacuated from the apparatus via line 6. If after reaction a mixture of oligomers is obtained, this last fraction is sent via line 7 to a zone where it undergoes a second separation step to isolate the desired products (recovered via line 8) from the $C_{(2n+1)}^+$ mixture evacuated via line 9.

The apparatus of FIGS. 2 and 3 are used when, as is preferable, the first step is a homogeneous type liquid phase catalytic oligomerization reaction.

FIG. 4 describes the case where the feed contains olefins containing n carbon atoms ($C_n$); n is generally 2, 3, 4, 5 or 6. In this case, the desired product is the dimer ($C_{2n}$). The expression $C_{(2n+1)}^+$ represents the olefins produced which have a carbon chain which is longer than that of the desired dimer.

In the embodiment shown in FIG. 4, the cut to be treated containing at least one olefin ($C_n$) is introduced via line 1 into reaction zone $R_1$ where in a first step it undergoes catalytic oligomerization, either of the liquid phase homogeneous type or of the heterogeneous type with a solid support. After the first reaction, the effluent is separated. The overhead fraction containing unreacted olefins is separated from the oligomer products using a separator $S_2$. If a mixture of oligomers is produced, the desired product still has to be separated from the mixture, and it is then sent to a second separator via line 12. The overhead fraction obtained in separator $S_2$ is sent via line 10 to a heat exchanger $E_1$ traversed by a cold liquid. After cooling to a temperature in the range about 15–30° C. to +60° C., preferably in the range –30° C. to +40° C., it is sent via line 3 second reaction zone $R_2$ where it undergoes liquid-liquid two-phase medium catalytic oligomerization. After washing, the hydrocarbon fraction is sent via line to separator $S_1$, the fraction containing unreacted olefins ($C_n$) is separated from the fraction containing the oligomer products. This fraction $C_n$ is evacuated from the apparatus via line 6. If after the reaction a mixture of oligomers is obtained, this last fraction is sent via line 7 to a zone where it undergoes a second separation to isolate the desired products (recovered via line 8) from the $C_{(2n+1)}^+$ mixture evacuated via line 9.

The apparatus of FIG. 4 is used, as is preferable, when the first step is a heterogeneous type catalytic oligomerization reaction using a solid support.

FIG. 5 shows a detail of reaction zone $R_2$ where liquid-liquid two-phase medium catalytic oligomerization is carried out. In FIG. 5, the feed containing at least one olefin is sent to reaction zone $R_2'$ via line 3. Line 16 supplies the reactor (or a series of reactors) with feed sent via line 3 and with alkylaluminium sent via line 20. After reaction, the effluent is sent via line 14 to a settler $D_1$ provided with a circulation pump for the reaction liquids. After settling, a supernatant phase is obtained which contains olefins and a denser polar phase which contains the catalyst. Before injecting the ionic phase into the reactor via line 17, a quantity of spent ionic phase is extracted via line 18 and replaced with the same quantity of fresh ionic phase introduced via line 19. A portion of the phase containing the olefins is recycled via line 15. It is pumped; then in all cases, it is cooled by means of heat exchanger $E_2$ traversed by a cold fluid. This phase is returned to reactor $R_2'$ via line 16 after having been enriched in alkylaluminium via line 20, then in fresh feed via line 3.

The following examples illustrate the invention without limiting its scope.

EXAMPLES

Example 1

This example used an apparatus corresponding to FIG. 2.

A flow of 10 kg/h of a feed comprising olefins containing 4 carbon atoms, 60% by weight of which was butenes and 40% by weight of which was n-butane, was converted to oligomers in a series of two reactors operating in a homogeneous liquid phase using a continuously injected soluble catalyst. The composition and method of manufacture of the catalyst used in this example are described in U.S. Pat. No. 4,716,239. The reaction was carried out at +45° C. and the pressure was 1.3 MPa; the butene conversion in this first step was 70% by weight.

The effluent was separated by distillation into two fractions. The first fraction comprised olefins containing 4 carbon atoms comprising 31% of unreacted butenes and 69% of n-butane; this fraction was distilled at a rate of 5.8 kg/h. The second fraction contained octenes and hydrocarbons with a carbon chain containing nine carbon atoms; its flow rate was 4.2 kg/h.

The octene yield with respect to the butenes introduced was 60% by weight.

The unreacted olefins containing 4 carbon atoms were brought to +10° C. using a heat exchanger then introduced into a reaction zone. The olefins were then injected into a 5 l volume reactor, under the following reaction conditions: a temperature of +10° C. and pressure of 0.7 MPa. After reaction, the effluent was sent to a 5 l volume settler provided with a reaction liquid circulation pump. After circulating using the pump, the effluent was cooled to a temperature of +10° C. using a heat exchanger traversed by a fluid (FIG. 5).

The reactor contained 1512 g of a polar phase comprising the following liquid catalytic composition: 746 g of aluminium chloride, 694 g of butylmethylimidazolium chloride and 72 g of nickel chloride.

1.2 g/h of a polar phase containing the catalyst was continuously extracted from the reaction zone and 1.2 g/h of a fresh polar phase with the same composition as that described above was continuously injected.

9.6 g/h of a 50% by weight dichloroethylaluminium chloride (DCEA) solution in hexane was also introduced into the reaction zone. This solution was evacuated with the effluent sent to the washing zone.

The phase containing the olefins was separated from the polar phase by settling, then combined with the oligomer phase produced in the first step. In order to eliminate the catalyst which is soluble in the product oligomer phase, the aggregate was treated with a basic aqueous solution then with water.

After washing, the different constituents were separated by distillation to recover hydrocarbons containing 4 carbon atoms at a rate of 4.36 kg/h. This fraction contained essentially butane (non reactive) and a small quantity of unreacted butenes. The heaviest fraction containing the desired octenes was then sent to a second separation zone from which octenes were recovered overhead at a rate of 1.30 kg/h and oligomers containing at least nine carbon atoms were recovered from the bottom at a rate of 0.14 kg/h.

The octene yield from the second step was 72% by weight, and the global octene yield was 81% by weight.

The sequence of processes of the invention had increased the relative octene gain by 35% over the traditional single step process.

Example 2

This example used an apparatus corresponding to FIG. 3.

A flow rate of 10 kg/h of a feed comprising olefins containing 4 carbon atoms, 80% by weight of which was butenes and 20% by weight of which was n-butane, was converted to oligomers in a series of two reactors operating in a homogeneous liquid phase. The catalyst used in this Example was described in U.S. Pat. No. 4,716,239 and was continuously injected. The reaction was carried out at +45° C. and the pressure was 1.3 MPa. The effluent was freed of dissolved catalyst by treatment with an aqueous basic solution then with water.

It was then separated into two fractions: the first fraction was distilled at a rate of 3.6 kg/h and comprised hydrocarbons containing 4 carbon atoms, 44% of which was unreacted butenes and 56% of which was n-butane. The second fraction contained the desired octenes and oligomers with a chain containing at least nine carbon atoms. This second fraction was then distilled to separate the octenes which were produced at a rate of 5.1 kg/h, and oligomers with a chain containing at least nine, carbon atoms which were produced at a rate of 1.3 kg/h.

The octene yield with respect to the butene introduced was 64% by weight.

The hydrocarbon fraction containing 4 carbon atoms was washed then azeotropically distilled to eliminate dissolved water. This fraction, brought to +10° C. using a heat exchanger, was then introduced into a reaction zone. The olefins were then injected into a 5 l volume reactor, and after reaction, the effluent was sent to a 5 l volume settler provided with a reaction liquid circulation pump. The reaction was carried out at +10° C. and at a pressure of 0.7 MPa. After circulating using the pump, the effluent was cooled to a temperature of +10° C. using a heat exchanger traversed by a fluid (FIG. 5).

The reactor contained 1260 g of a polar phase in which the catalyst was dissolved. The liquid catalytic composition was as follows: 622 g of aluminium chloride, 578 g of butylmethylimidazolium chloride and 60 g of nickel chloride.

1.0 g/h of polar phase containing the catalyst was continuously extracted from the reaction zone and 1.0 g/h of a fresh polar phase with the same composition as that described above was continuously injected.

7.2 g/h of a 50% by weight dichloroethylaluminium chloride (DCEA) solution in hexane was also introduced into the reaction zone and eliminated with the effluent. This solution was evacuated with the effluent sent to the washing zone.

The phase containing the olefins was separated from the polar phase in the settler then treated with a basic aqueous solution then with water.

This phase was distilled to recover hydrocarbons containing 4 carbon atoms containing essentially butane (non reactive) and a small quantity of unreacted butenes, at a rate of 2.32 kg/h. The heaviest fraction containing the desired octenes was then sent to a second separation zone from which octenes were recovered overhead at a rate of 1.15 kg/h and oligomers containing at least nine carbon atoms were recovered from the bottom at a rate of 0.13 kg/h.

The octene yield from the second step was 72% by weight, and the global octene yield was 78% by weight.

The relative gain of octenes had been increased by 22% by the sequence of processes of the invention over the traditional single step process.

Example 3

This example used an apparatus corresponding to FIG. 4.

A flow rate of 10 kg/h of a feed comprising olefins containing 4 carbon atoms, 80% by weight of which was butenes and 20% by weight of which was n-butane, was converted to oligomers in a fixed bed reactor using a catalyst containing nickel sulphate deposited on alumina. The catalyst and its method of manufacture are described in French application No. 2,608,594. The butene conversion was 70% and the selectivity for octenes was 75%, giving an octene yield of 52.5%. The reaction was carried out at +50° C. and the pressure was 1.3 MPa. The hourly space velocity was 0.8 $h^{-1}$.

The effluent was then separated into two fractions by distillation: a fraction comprising hydrocarbons containing 4 carbon atoms was obtained, comprising 55% of unreacted butenes and 45% of n-butane (unreactive), at a rate of 4.4 kg/h, and 5.6 kg/h of an oligomer fraction was also obtained oligomers with a chain containing at least eight carbon atoms.

The fraction of olefins containing 4 carbon atoms brought to a temperature of +10° C. using a heat exchanger was then introduced into a reaction zone comprising a 5 l reactor, behind which was placed a 5 l volume settler provided with a pump for circulating settled liquid. After starting up the pump, the effluent was cooled to a temperature of +10° C. using a heat exchanger traversed by a fluid (FIG. 5). The reaction was carried out at +10° C. and at a pressure of 0.7 MPa.

The reactor contained 1260 g of a polar phase in which the liquid catalyst with the following composition was dissolved: 622 g of aluminium chloride, 578 g of butylmethylimidazolium chloride and 60 g of nickel chloride.

1.0 g/h of a polar phase containing the catalyst was continuously extracted from the reaction zone and 1.0 g/h of a fresh polar phase with the same composition as that described above was continuously injected.

7.2 g/h of a 50% by weight dichloroethylaluminium chloride (DCEA) solution in hexane was also introduced into the reaction zone. This solution was evacuated with the effluent sent to the washing zone.

The effluent, separated by settling the polar phase in the settler, was then treated with a basic aqueous solution then with water.

It was separated by distillation to recover a hydrocarbon fraction containing 4 carbon atoms containing essentially butane and a small quantity of butenes, at a rate of 2.48 kg/h. The heaviest fraction containing the desired octenes was then sent to a second separation zone from which octenes were recovered overhead at a rate of 1.73 kg/h and oligomers containing at least nine carbon atoms were recovered from the bottom at a rate of 0.19 kg/h.

The global octene yield was 74% by weight.

The sequence of processes of the invention had increased the relative octene gain by 41% over the traditional single step process.

Example 4

This example used an apparatus corresponding to FIG. 4.

A flow rate of 8.2 kg/h of a feed comprising olefins containing 4 carbon atoms, 87.4% by weight of which was butenes, with 10.1% by weight of butane and 2.5% by weight of isobutane, was converted to oligomers in a fixed bed catalysis reaction (carried out in two reactors of 5 and 10 l in series). The reaction was carried out at +100° C. and the pressure was 3 MPa. The hourly space velocity was 1 $h^{-1}$.

The catalyst used, based on silica-alumina, is sold by IFP Enterprise under the trade reference IP501.

The effluent was then separated into two fractions by distillation: a fraction comprising hydrocarbons containing 4 carbon atoms was obtained, comprising 35.7% of unreacted butenes at a rate of 1.6 kg/h, and a fraction containing oligomers. This last fraction was then separated into a gasoline fraction (with the following specifications: initial point 35° C. and 95% point distilling at 230° C.) obtained at a rate of 6.27 kg/h and into a heavy fraction at a rate of 0.33 kg/h.

The fraction of olefins containing 4 carbon atoms, brought to a temperature of +10° C. using a heat exchanger traversed by a cold liquid, was then introduced into a 2 l volume reactor. The reaction was carried out at +10° C. and at a pressure of 0.7 MPa. After reaction, the effluent was introduced into a 2 l volume settler provided with a pump for circulating the organic phase. After pumping, the effluent was cooled to a temperature of +10° C. using a heat exchanger traversed by a fluid (FIG. 5).

The reactor contained 525 g of a polar phase containing the liquid catalyst which had the following composition: 259 g of aluminium chloride, 241 g of butylmethylimidazolium chloride and 25 g of nickel chloride.

0.5 g/h of polar phase containing the catalyst was continuously extracted from the reaction zone and 0.5 g/h of a fresh polar phase with the same composition as that described above was continuously injected.

4.8 g/h of a 25% by weight dichloroethylaluminium chloride (DCEA) solution in hexane was also introduced into the reaction zone. This solution was evacuated with the effluent sent to the washing zone.

The effluent separated by settling the polar phase in the settler was then treated with a basic aqueous solution then with water.

It was separated by distillation to recover a hydrocarbon fraction containing 4 carbon atoms comprising essentially butane (unreactive) and 10% by weight of unreacted butenes, at a rate of 1.15 kg/h, and a fraction containing the oligomers. The latter fraction was then separated into a gasoline fraction (with the following specifications: an initial point of 35° C. and a 95% point distilling at 230° C.) obtained at a rate of 0.45 kg/h, and into a heavy fraction.

The total quantity of gasoline formed was 6,72 kg/h. The gasoline yield was 93.7%.

The combination of two oligomerization reactions enabled the gasoline yield to be increased and the butene content to be decreased from 35.7% to 10% of the residual hydrocarbon feed containing 4 carbon atoms.

In the appended claims, the expression "slightly miscible with the organic phase" means that the miscibility is not more than about 3%, preferably not more than 1%, the percentages referring to the percent of the medium with an ionic nature soluble in the organic phase at 25° C.

The preceding examples can be repeated with similar success by substituting the generically or specifically described reactants and/or operating conditions of this invention for those used in the preceding examples.

The entire disclosure of all applications, patents and publications, cited above, and of corresponding French application No. 97/08633 filed Jul. 4, 1997, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for oligomerizing an organic feed containing at least one olefin, comprising subjecting said feed to at least two successive oligomerizations with different catalysts, at least one oligomerization being conducted with a homogeneous catalyst in a liquid-liquid two-phase medium containing an ionic liquid, with the proviso that the homogeneous catalyst does not contain a phosphine.

2. A process according to claim 1, comprising a first and a second oligomerization, the second oligomerization being conducted in the presence of at least one catalytic element in a liquid-liquid two-phase medium containing an ionic liquid.

3. A process according to claim 1, wherein the organic feed contains at least one olefin the chain of which contains two to six carbon atoms, or a mixture of such olefins.

4. A process according to claim 2, comprising introducing a portion of the organic feed which has not reacted in the first oligomerization, optionally after a catalyst inhibiting treatment, into the two-phase medium at a temperature of about −50° C. to +10° C. and at a pressure of about 0.01 MPa to 20 MPa, stirring being at least partially carried out by circulating a mixture of two reaction liquids in a loop, to produce an effluent, and settling said effluent after reaction.

5. A process according to claim 1, wherein the catalyst used for oligomerization in a two-phase medium is a nickel complex or a mixture of nickel complexes, and the ionic liquid comprises at least one salt with formula $Q^+A^-$, where $Q^+$ is a quaternary ammonium or phosphonium cation or a mixture of the two or a lithium cation, and $A^-$ is a co-ordinating or non co-ordinating anion.

6. A process according to claim 5, in which the anion is a halogenoaluminate, an organohalogenoaluminate, an organogallate, an organohalogenogallate or a mixture thereof.

7. A process according to claim 4, wherein after undergoing oligomerization in a two-phase medium and settling the effluent, the effluent is washed and oligomer products are separated from unreacted hydrocarbons.

8. A process according to claim 1, in which an effluent obtained after the first oligomerization is washed, oligomer products thus produced are isolated, the compounds which have not reacted are dried before undergoing oligomerization in a liquid-liquid two-phase medium in a second reaction.

9. A process according to claim 8, wherein the first and the second oligomerization are each followed by washing, a washing step which follows the first oligomerization being carried out in the same zone as a washing step following the two-phase medium oligomerization.

10. A process for oligomerizing an organic feed according to claim 1, wherein the first oligomerization is carried out by homogeneous liquid phase catalysis.

11. A process for oligomerizing an organic feed according to claim 10, wherein in the first oligomerization, the catalyst is a nickel compound or a mixture of nickel compounds, with a co-catalyst which is an alkylaluminum or a mixture of alkylaluminum compounds or a halogenoalkylaluminum or a mixture of halogenoalkylaluminum compounds.

12. A process for oligomerizing an organic feed according to claim 10, comprising employing a catalyst additive which is a compound with an acidic nature or a corresponding anion, a carboxylic acid ester, an epoxy compound or a mixture thereof.

13. A process according to claim 10 in which, in the first oligomerization the olefin or olefins to be treated are continuously introduced into a reaction zone which is continuously supplied with catalytic composition at a temperature of about −40° C. to +100° C., at a pressure such that the reactants are kept at least partially in the liquid phase and under stirring conditions suitable for obtaining maximum conversion of the feed to dimers, co-dimers, oligomers or a mixture thereof.

14. A process for oligomerizing an organic feed according to claim 1, wherein the first oligomerization is heterogeneous catalysis using a solid catalyst.

15. A process according to claim 14, wherein the catalyst used in the heterogeneous catalysis is a nickel compound on a support, or a support alone.

16. A process according to claim 14, having a reaction temperature of oligomerization about +10° C. to +250° C., and a pressure such that the feed is at least partially in the liquid state.

17. A process according to claim 1, wherein the organic phase consists essentially of aliphatic hydrocarbons.

18. A process according to claim 2, wherein the organic phase consists essentially of aliphatic hydrocarbons.

19. A process according to claim 5, wherein the organic phase consists essentially of aliphatic hydrocarbons.

20. A process according to claim 6, wherein the organic phase consists essentially of aliphatic hydrocarbons.

21. A process according to claim 1, wherein the organic feed contains at least one olefin the chain of which contains three to six carbon atoms, or a mixture of such olefins.

22. A process for oligomerizing an organic feed containing at least one olefin, comprising subjecting said feed to at least two successive oligomerizations with different catalysts, at least one oligomerization being conducted with a homogeneous catalyst in a liquid-liquid two-phase medium containing an ionic liquid, wherein after a first oligomerization unreacted feed is separated and subjected to a second oligomerization, with the proviso that the homogeneous catalyst does not contain a phosphine.

23. A process according to claim 22, comprising a first and a second oligomerization, the second oligomerization being conducted in the presence of at least one catalytic element in a liquid-liquid two-phase medium containing an ionic liquid.

24. A process according to claim 22, wherein the catalyst used for oligomerization in a two-phase medium is a nickel complex or a mixture of nickel complexes, and the ionic liquid comprises at least one salt with formula $Q^+A^-$, where $Q^+$ is a quaternary ammonium or phosphonium cation or a mixture of the two or a lithium cation, and $A^-$ is a coordinating or non co-ordinating anion.

25. A process according to claim 22, in which an effluent obtained after the first oligomerization is washed, oligomer products thus produced are isolated, and compounds which have not reacted are dried before undergoing oligomerization in a liquid-liquid two-phase medium in a second reaction.

26. A process according to claim 25, wherein the first and the two-phase medium oligomerization are each followed by washing, a washing step which follows the first oligomerization being carried out in the same zone as a washing step following the two-phase medium oligomerization.

* * * * *